United States Patent [19]

Iuchi et al.

[11] Patent Number: 5,126,222
[45] Date of Patent: Jun. 30, 1992

[54] ELECTROPHOTOGRAPHIC PHOTOSENSITIVE MEMBER CONTAINING A BARBITURIC ACID OR THIOBARBITURIC ACID DERIVATIVE

[75] Inventors: Kazushi Iuchi; Shintetsu Go; Hajime Miyazaki, all of Yokohama; Toshie Miyaji, Kawasaki, all of Japan

[73] Assignee: Canon Kabushiki Kaisha, Tokyo, Japan

[21] Appl. No.: 535,476

[22] Filed: Jun. 11, 1990

[30] Foreign Application Priority Data

Jun. 12, 1989 [JP] Japan .................................. 1-46864
Jun. 12, 1989 [JP] Japan ................................. 1-146863

[51] Int. Cl.$^5$ ............................................. G03G 5/06
[52] U.S. Cl. ........................................ 430/58; 430/76; 430/78; 355/200
[58] Field of Search ................... 430/58, 73, 78, 79, 430/76; 355/200

[56] References Cited

U.S. PATENT DOCUMENTS 4,395,473  7/1983  Horie et al. ......................... 430/58
4,500,622  2/1985  Horie et al. ......................... 430/58

Primary Examiner—John Goodrow
Attorney, Agent, or Firm—Fitzpatrick, Cella, Harper & Scinto

[57] ABSTRACT

An electrophotographic photosensitive member comprises a conductive support and a photosensitive layer provided thereon, wherein said photosensitive layer contains at least one of the compounds of the following Formula (I) and (II).

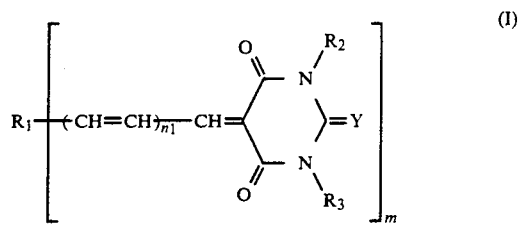

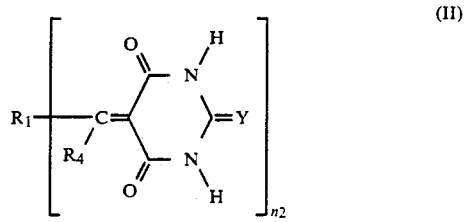

wherein Y represents an oxygen atom or a sulfur atom; $R_1$ represents a substituted or unsubstituted aromatic hydrocarbon group or aromatic heterocyclic group which may be bonded through a bonding group; $R_2$ and $R_3$ each represent a hydrogen atom, a substituted or unsubstituted alkyl group or aryl group; m is an integer of 1, 2 or 3; $n_2$ is an integer of 1, 2 or 3; $R_4$ represents a hydrogen atom, an alkyl group or a substituted or unsubstituted phenyl group; and $n_2$ is an integer of 1, 2 or 3.

8 Claims, 1 Drawing Sheet

ELECTROPHOTOGRAPHIC PHOTOSENSITIVE MEMBER CONTAINING A BARBITURIC ACID OR THIOBARBITURIC ACID DERIVATIVE

BACKGROUND OF THE INVENTION

1. Field of the Invention

The present invention relates to an electrophotographic photosensitive member. More particularly, it relates to an electrophotographic photosensitive member comprising a photosensitive layer containing a barbituric acid derivative or thiobarbituric acid derivative having a specific structure.

2. Related Background Art

Inorganic photoconductive materials such as selenium, cadmium sulfide and zinc oxide have been hitherto used in electrophotographic photosensitive members.

On the other hand, electrophotographic photosensitive members comprised of an organic photoconductive material are known to include those comprised of a photoconductive polymer as typified by poly-N-vinylcarbazole or a low-molecular organic photoconductive material such as 2,5-bis(p-diethylaminophenyl)-1,3,4-oxadiazole, and also those comprised of a combination of such an organic photoconductive material and a dye or pigment of various types.

The electrophotographic photosensitive members comprised of an organic photoconductive material have the advantages that they have good film forming properties so that they can be produced by coating, and much higher productivity so they can be provided at a low cost. They have also the advantages such that color sensitivity can be freely controlled by selecting sensitizers such as dyes or pigments used. Accordingly, studies have been hitherto made thereon over a wide range. Particularly in recent years, development of a function-separated photosensitive member comprising a lamination of a charge generation layer containing an organic photoconductive dye or pigment and a charge transport layer containing the above-mentioned photoconductive polymer or low-molecular organic photoconductive material has brought about remarkable improvements in the sensitivity and durability in respect of which the conventional organic electrophotographic photosensitive members have been considered to have disadvantages.

Materials that exhibit such photoconductivity are known to include, for example, azo pigments, and a barbituric acid derivative or thiobarbituric acid derivative as disclosed in Japanese Patent Application Laid-Open No. 57-119355.

Electrophotographic photosensitive members in which a conventional disazo pigment or a barbituric acid derivative or thiobarbituric acid derivative is used, however, are not satisfactory in view of sensitivity, and potential stability in repeated use. Thus, only a very few materials have been put into practical use.

SUMMARY OF THE INVENTION

An object of the present invention is to provide a novel photoconductive material.

Another object of the present invention is to provide an electrophotographic photosensitive member having high-sensitivity characteristics satisfactory for practical use and potential characteristics stable in repeated use.

Still another object of the present invention is to provide an electrophotographic apparatus equipped with such an electrophotographic photosensitive member.

According to an aspect of the present invention, there is provided an electrophotographic photosensitive member comprising a conductive support and a photosensitive layer provided thereon, wherein said photosensitive layer contains a barbituric acid derivative or a thiobarbituric acid derivative represented by the following Formula (I) or (II).

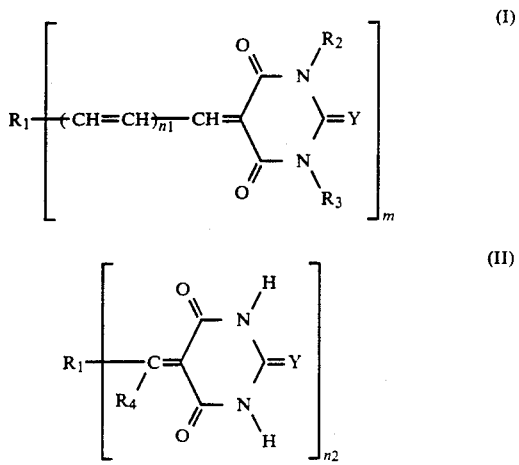

wherein Y represents an oxygen atom or a sulfur atom; $R_1$ represents a substituted or unsubstituted aromatic hydrocarbon group or aromatic heterocyclic group which may be bonded through a bonding group; $R_2$ and $R_3$ each represent a hydrogen atom, a substituted or unsubstituted alkyl group or aryl group; m is an integer of 1, 2 or 3; $n_1$ is an integer of 1, 2 or 3; $R_4$ represents a hydrogen atom, an alkyl group or a substituted or unsubstituted phenyl group; and $n_2$ is an integer of 1, 2 or 3.

The electrophotographic photosensitive member of the present invention employs in a charge generation layer the barbituric acid derivative or thiobarbituric acid derivative represented by Formula (I) or (II), and exhibits a remarkable effect that it has a high sensitivity and a superior potential stability in repreated use.

DESCRIPTION OF THE PREFERRED EMBODIMENTS

Figure 1:
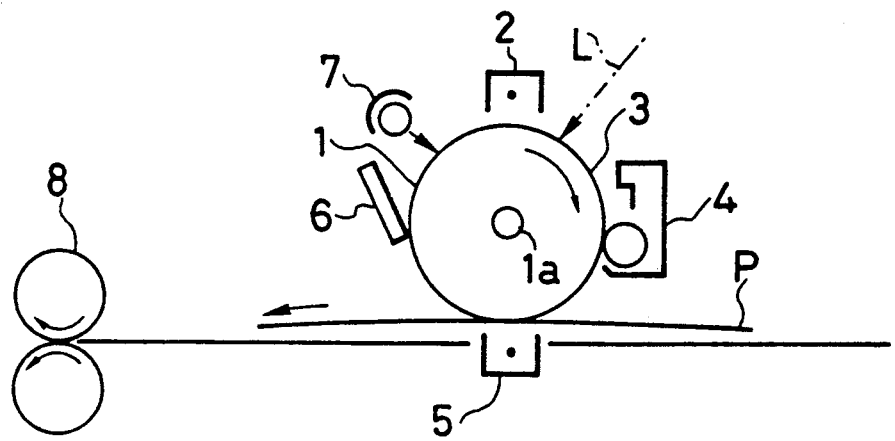
FIG. 1 schematically illustrates the constitution of a general, transfer-type electrophotographic apparatus in which an electrophotographic photosensitive member of the present invention is used.

The present invention will be described below in detail.

In the definition for $R_1$ in the above Formulas (I) and (II), the bonding group includes a carbonyl group, an imino group and a nitrilo group. The aromatic hydrocarbon group includes a phenyl group, a naphthyl group, a phenanthryl group, an anthranyl group and a pyrenyl group. The aromatic heterocyclic group includes a pyridyl group, a thienyl group, a thiazolyl group, a carbazolyl group, a benzimidazolyl group, a benzothiazolyl group, a furyl group, and a quinolyl group. In the definitions for $R_2$ and $R_3$, the alkyl group includes a methyl group and an ethyl group. The aryl group includes a phenyl group, a naphthyl group and a tosyl group. The substituent for these groups includes halogen atoms such as a chlorine atom and a bromine atom, alkyl groups such as a methyl group and an ethyl group, aryl groups such as a phenyl group, a naphthyl group and an anthryl group, aralkyl groups such as a benzyl group and a phenethyl group.

$R_4$ represents a hydrogen atom, an alkyl group or a substituted or unsubstituted phenyl group, and $n_2$ is an integer of 1, 2 or 3.

In the definition for $R_4$, the alkyl group includes a methyl group and an ethyl group. The substituent for these groups includes halogen atoms such as a chlorine atom and a bromine atom, alkyl groups such as a methyl group and an ethyl group, aryl groups such as a phenyl group, a naphthyl group and an anthryl group, an aralkyl groups such as a benzyl group and a phenethyl group.

Typical examples of the barbituric acid derivative or thiobarbituric acid derivative used in the present invention, represented by Formulas (I) or (II), are shown below. Materials used in the present invention, however, are by no means limited to these.

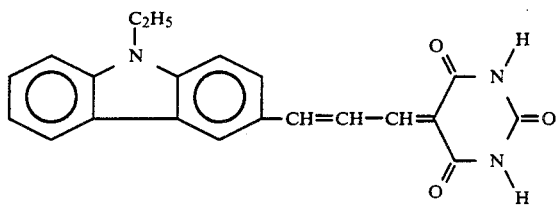

Compound I-(1)

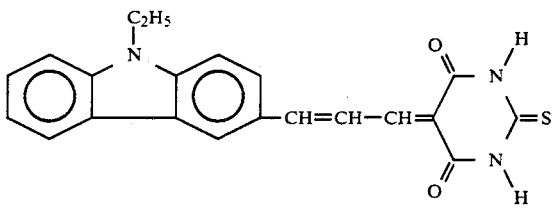

Compound I-(2)

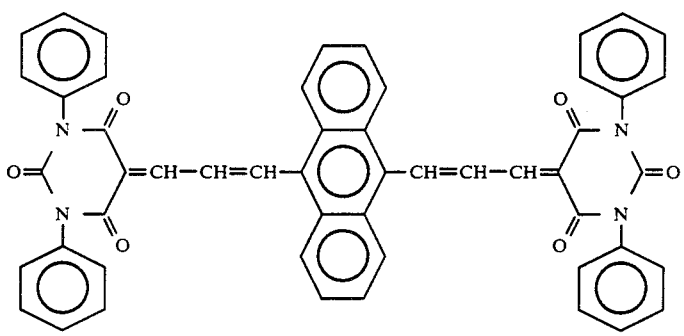

Compound I-(3)

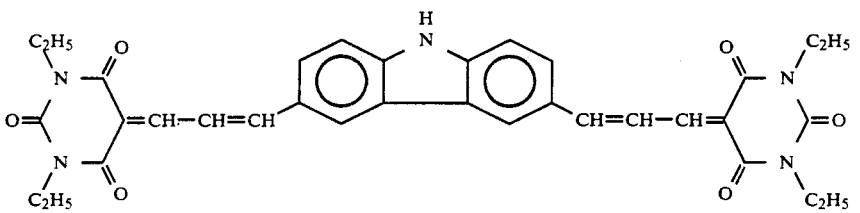

Compound I-(4)

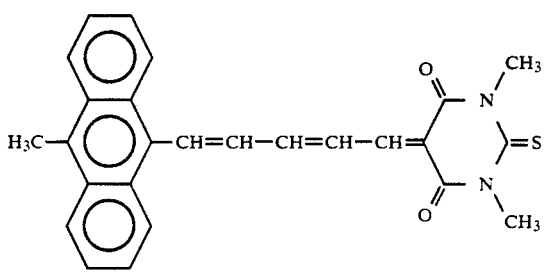

Compound I-(5)

-continued
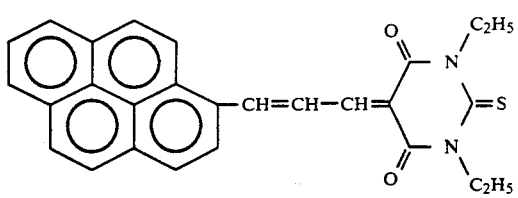
Compound I-(6)
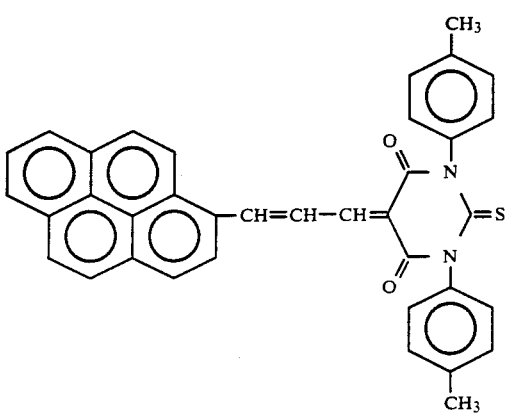
Compound I-(7)
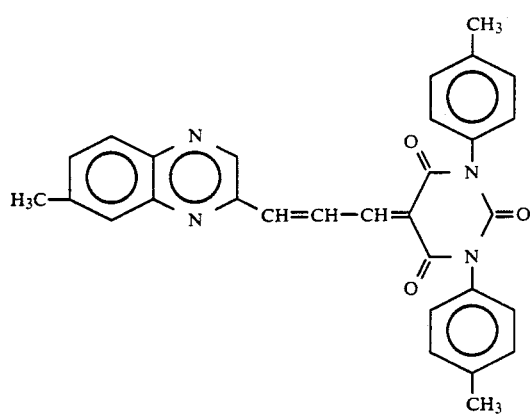
Compound I-(8)
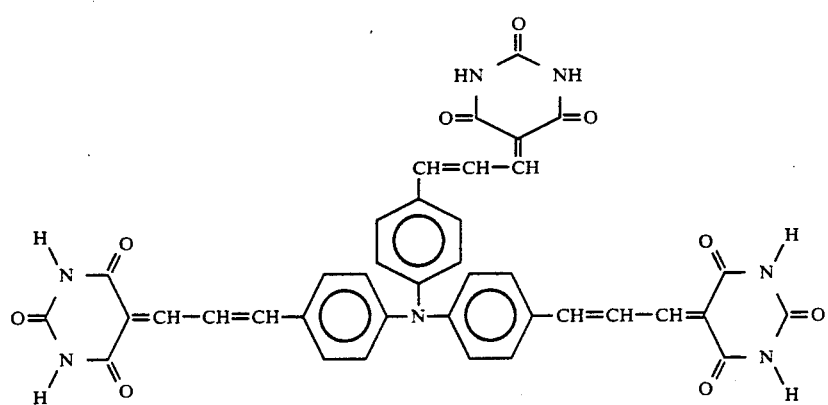
Compound I-(9)

-continued
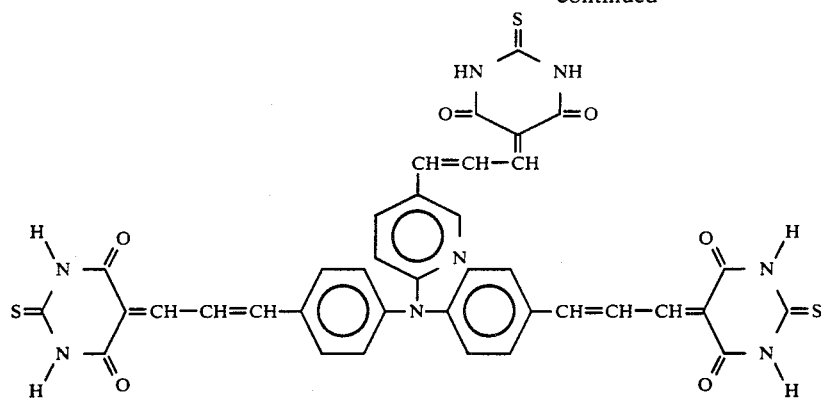
Compound I-(10)
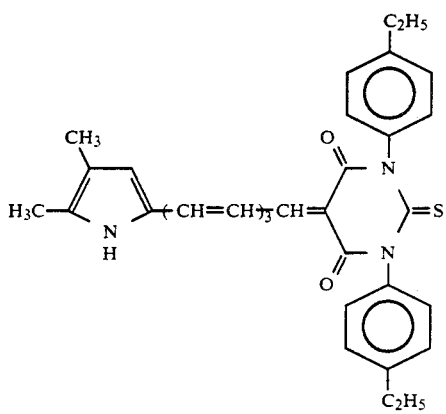
Compound I-(11)
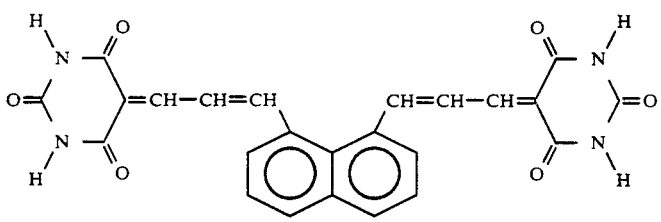
Compound I-(12)
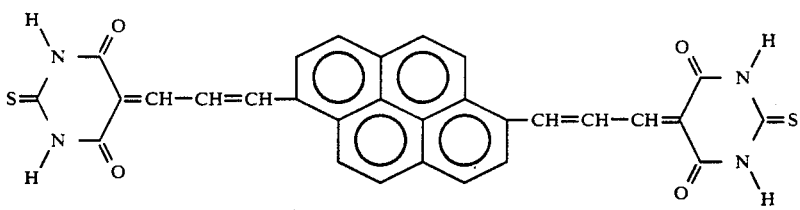
Compound I-(13)
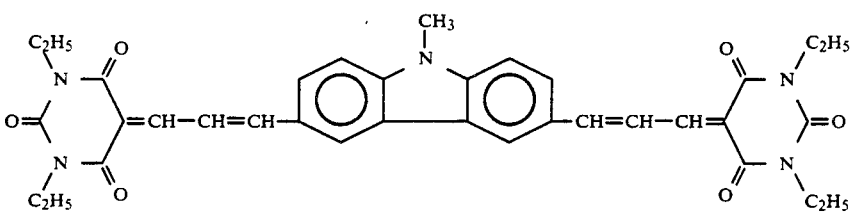
Compound I-(14)
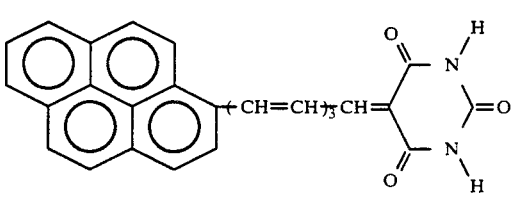
Compound I-(15)

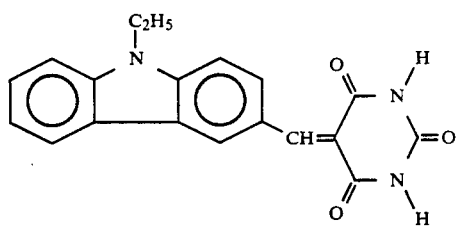
Compound II-(1)
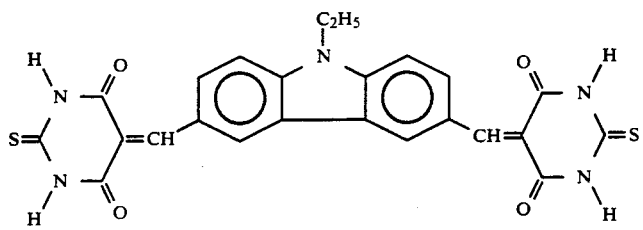
Compound II-(2)
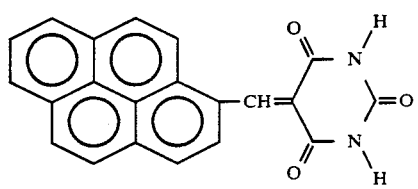
Compound II-(3)
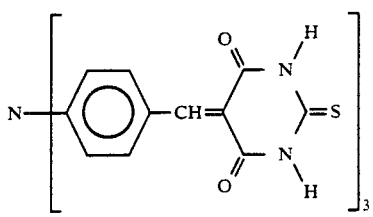
Compound II-(4)
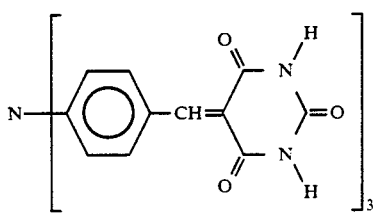
Compound II-(5)
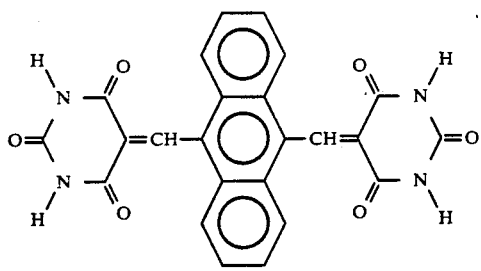
Compound II-(6)
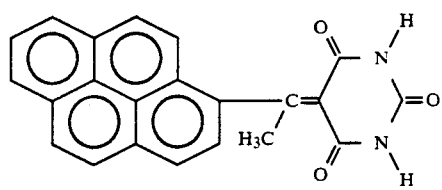
Compound II-(7)

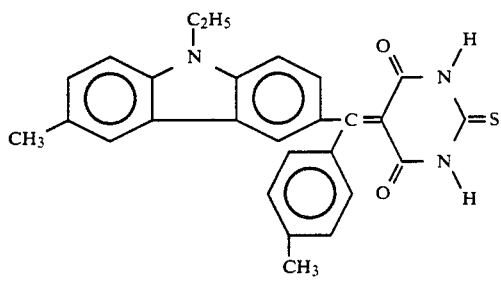

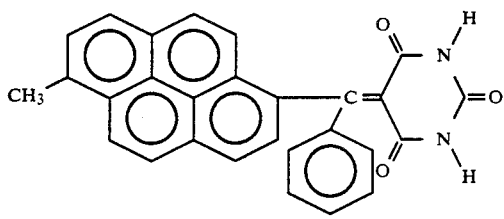

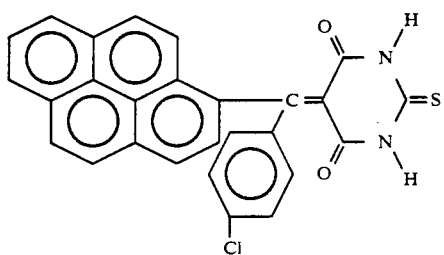

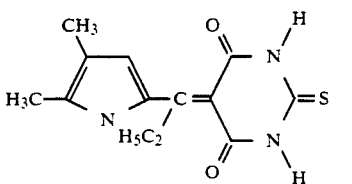

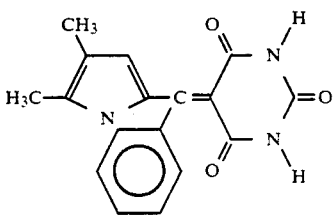

Compound II-(8)

Compound II-(9)

Compound II-(10)

Compound II-(11)

Compound II-(12)

SYNTHESIS EXAMPLE

Synthesis of Compound I-(2):

In 50 ml of an eggplant type flask, 2.1 g of the following aldehyde compound and 30 ml of ethanol were added, followed by heating to 60° C.

Next, 1.0 g of thiobarbituric acid was added, and the mixture was stirred at 60° C. for 4 hours.

The resulting reaction mixture was cooled to room temperature, filtered, washed with methanol, and then dried. The desired Compound I-(2) of the present invention was thus obtained. Yield: 1.3 g. Aldehyde compound:

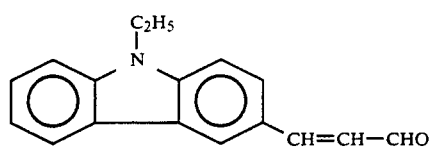

Elementary analysis:

|   | Calculated (%) | Found (%) |
|---|---|---|
| C | 64.88 | 64.94 |
| H | 4.90 | 4.88 |
| N | 11.95 | 11.96 |

SYNTHESIS EXAMPLE

Synthesis of Compound II-(3):

In 50 ml of an eggplant type flask, 1.85 g of 1-pyrene aldehyde and 30 ml of ethanol were added, followed by heating to 60° C.

Next, 1.0 g of barbituric acid was added, and the mixture was stirred at 60° C. for 6 hours.

The resulting reaction mixture was cooled to 0° C., filtered, washed with methanol, and then dried. The Compound II-(3) of the present invention was thus obtained. Yield: 1.1 g.

Elementary analysis:

|   | Calculated (%) | Found (%) |
| --- | --- | --- |
| C | 74.01 | 74.11 |
| H | 3.60 | 3.55 |
| N | 8.22 | 8.23 |

The electrophotographic photosensitive member of the present invention comprises a conductive support and, provided thereon, a photosensitive layer containing the barbituric acid derivative or thiobarbituric acid derivative represented by Formula (I) or (II) (hereinafter "the general formula").

The photosensitive layer may be of any known form, but it is particularly preferred to be a photosensitive layer of a function-separated type comprising a lamination of a charge generation layer comprised of a photosensitive layer containing the compound represented by the general formula, and a charge transport layer containing a charge-transporting material.

The charge generation layer can be formed by coating on a conductive support by a known method, a coating solution obtained by dispersing the compound represented by the general formula in a suitable binder together with a binder resin. The layer may be desirably a thin film layer having a coating thickness of, for example, not more than 5 $\mu$m, and preferably from 0.1 to 1 $\mu$m.

The binder resin used here may be selected from a vast range of insulating resins or organic photoconductive polymers, which may preferably include polyvinyl butyral, polyvinyl benzal, polyarylates, polycarbonates, polyesters, phenoxy resins, cellulose resins, acrylic resins, and urethane resins. These may be used in an amount of not more than 80% by weight, and preferably not more than 40% by weight, in terms of the content in the charge generation layer.

The solvent used may preferably be selected from materials that can dissolve the above resins and may not dissolve the charge transport layer or subbing layer which will be described later.

The solvent specifically includes ethers such as tetrahydrofuran, and 1,4-dioxane; ketones such as cyclohexanone, and methyl ethyl ketone; amides such as N,N-dimethylformamide; esters such as methyl acetate, and ethyl acetate; aromatic compounds such as toluene, xylene, and chlorobenzene; alcohols such as methanol, ethanol, and 2-propanol; and aliphatic halogenated hydrocarbons such as chloroform, methylene chloride, dichloroethylene, carbon tetrachloride, and trichloroethylene.

The charge transport layer is laminated above or below the charge generation layer, and has a function of receiving charge carriers from the charge generation layer in the presence of an electric field and transporting them to the surface.

The charge transport layer can be formed by coating a solution obtained by dissolving a charge-transporting material in a solvent optionally together with a suitable binder. It may have a coating thickness of usually from 5 to 40 $\mu$m, and preferably from 15 to 30 $\mu$m.

The charge-transporting material comprises an electron-transporting material and a hole-transporting material. The electron-transporting material includes, for example, electron attractive materials such as 2,4,7-trinitrofluorenone, 2,4,5,7-tetranitrofluorenone, chloranil, and tetracyanoquinodimethane, or these electron attractive materials formed into polymers.

The hole-transporting material includes polycyclic aromatic compounds such as pyrene, and anthracene; heterocyclic compounds of a carbazole type, indole type, imidazole type, oxazole type, thiazole type, oxathiazole type, pyrazole type, pyrazoline type, thiadiazole type or triazole type; hydrazone compounds such as p-diethylaminobenzaldehyde-N,N-diphenylhydrazone, and N,N-diphenylhydrazino-3-methylidene-9-ethylcarbazole; styryl compounds such as α-phenyl-4'-N,N-diphenylaminostilbene, 5-[4-(di-p-tolylamino)benzylidene-5H-dibenzo-[a,d]cycloheptene]; benzidine compounds; triarylmethane compounds; triphenylamines; or polymers having a group comprised of any of these compounds in the backbone chain or side chain, as exemplified by poly-N-vinylcarbazole and polyvinyl anthracene.

In addition to these organic charge-transporting materials, it is also possible to use inorganic materials such as selenium, selenium-tellurium, amorphous silicon, and cadmium sulfide.

These charge-transporting materials can be used alone or in combination of two or more kinds.

In instances in which the charge-transporting material has no film-forming properties, a suitable binder resin may be used, which specifically includes insulating resins such as acrylic resins, polyarylates, polyesters, polycarbonate, polystyrene, an acrylonitrile/styrene copolymer, polyacrylamides, polyamides, and chlorinated rubber; and organic photoconductive polymers such as poly-N-vinyl carbazole, and polyvinyl anthracene.

The conductive support may be formed of a metal as exemplified by aluminum, an aluminum alloy, copper, zinc, stainless steel, titanium, nickel, indium, gold, or platinum.

It is also possible to use a plastic support on which a film of such a metal is formed by vacuum deposition, a support made of a plastic or metallic support covered with conductive particles (e.g., carbon black, silver particles) together with a suitable binder resin, or a support made of plastic or paper impregnated with conductive particles.

A subbing layer having a barrier function and an adhesive function can also be provided between the conductive support and the photosensitive layer.

The subbing layer can be formed of casein, polyvinyl alcohol, nitrocellulose, a polyamide (such as nylon 6, nylon 66, nylon 610, copolymer nylon, or alkoxymethylated nylon), a polyurethane, or aluminum oxide.

It is suitable for the subbing layer to have a film thickness of not more than 5 $\mu$m, and preferably from 0.1 to 3 $\mu$m.

As another embodiment, the photosensitive member of the present invention includes an electrophotographic photosensitive member in which the compound represented by the general formula and the charge-transporting material are contained in the same layer. In such an embodiment, a charge-transfer complex comprised of poly-N-vinylcarbazole and trinitrofluorenone may also be used as the charge-transporting material.

The electrophotographic photosensitive member according to such an embodiment can be formed by coating a support with a solution obtained by dispersing the compound represented by the general formula and the charge-transporting material in a suitable resin solution, followed by drying.

In any electrophotographic photosensitive members, the compound represented by the general formula may be any of amorphous and crystalline forms. It is also possible, if necessary, to use the compound represented by the general formula, in combination of two or more kinds or in combination with a known charge-generating material.

The electrophotographic photosensitive member of the present invention can be not only utilized in electrophotographic copying machines, but also widely used in the fields to which electrophotography is applied, as exemplified by laser beam printers, CRT printers, LED printers, liquid crystal printers, and laser lithography.

FIG. 1 schematically illustrates an example of the constitution of a transfer electrophotographic apparatus in which a drum photosensitive member according to the present invention is used.

In FIG. 1, the numeral 1 denotes a drum photosensitive member serving as an image supporting member, which is rotated around a shaft 1a at a given peripheral speed in the direction shown by the arrow. In the course of rotation, the photosensitive member 1 is uniformly charged on its periphery, with positive or negative given potential by the operation of a charging means 2, and then imagewise exposed to light L (slit exposure, laser beam scanning exposure, etc.) at an exposure area 3 by the operation of an imagewise exposure means (not shown). As a result, electrostatic latent images corresponding to the exposure images are successively formed on the periphery of the photosensitive member.

The electrostatic latent images thus formed are subsequently developed by toner by the operation of a developing means 4. The resulting toner-developed images are then successively transferred by the operation of a transfer means 5, to the surface of a transfer medium P fed from a paper feed section (not shown) to the part between the photosensitive member 1 and the transfer means 5 in the manner synchronized with the rotation of the photosensitive member 1.

The transfer medium P on which the images have been transferred is separated from the surface of the photosensitive member and led through an image-fixing means 8, where the images are fixed and then delivered to the outside as a transcript (a copy).

The surface of the photosensitive member 1 after the transfer of images is brought to removal of the toner remaining after the transfer, using a cleaning means 6. Thus the photosensitive member is cleaned on its surface, subjected to removal of charges by means of a pre-exposure means 7, and then repeatedly used for the formation of images.

The charging means 2 for giving uniform charge on the photosensitive member 1 include corona chargers, which are commonly put into wide use. As the transfer means 5, corona transfer units are also commonly put into wide use.

In the electrophotographic apparatus, plural components from among the constituents such as the above photosensitive member, developing means and cleaning means may be combined as one apparatus unit so that the unit can be freely mounted on or detached from the body of the apparatus. For example, the photosensitive member 1 and the cleaning means 6 may be joined into one apparatus unit so that the unit can be freely mounted or detached using a guide means such as a rail provided in the body of the apparatus. Here, the above apparatus unit may be so constituted as to be joined together with the charge means and/or the developing means.

In the case when the electrophotographic apparatus is used as a copying machine or a printer, optical image exposure to light L is performed by reading of light reflected from, or transmitted through an original, or the original itself, conversion of the light read to a signal, scanning of a laser beam according to the signal, and driving of an LED array, or driving of a liquid crystal shutter array.

Figure 2:
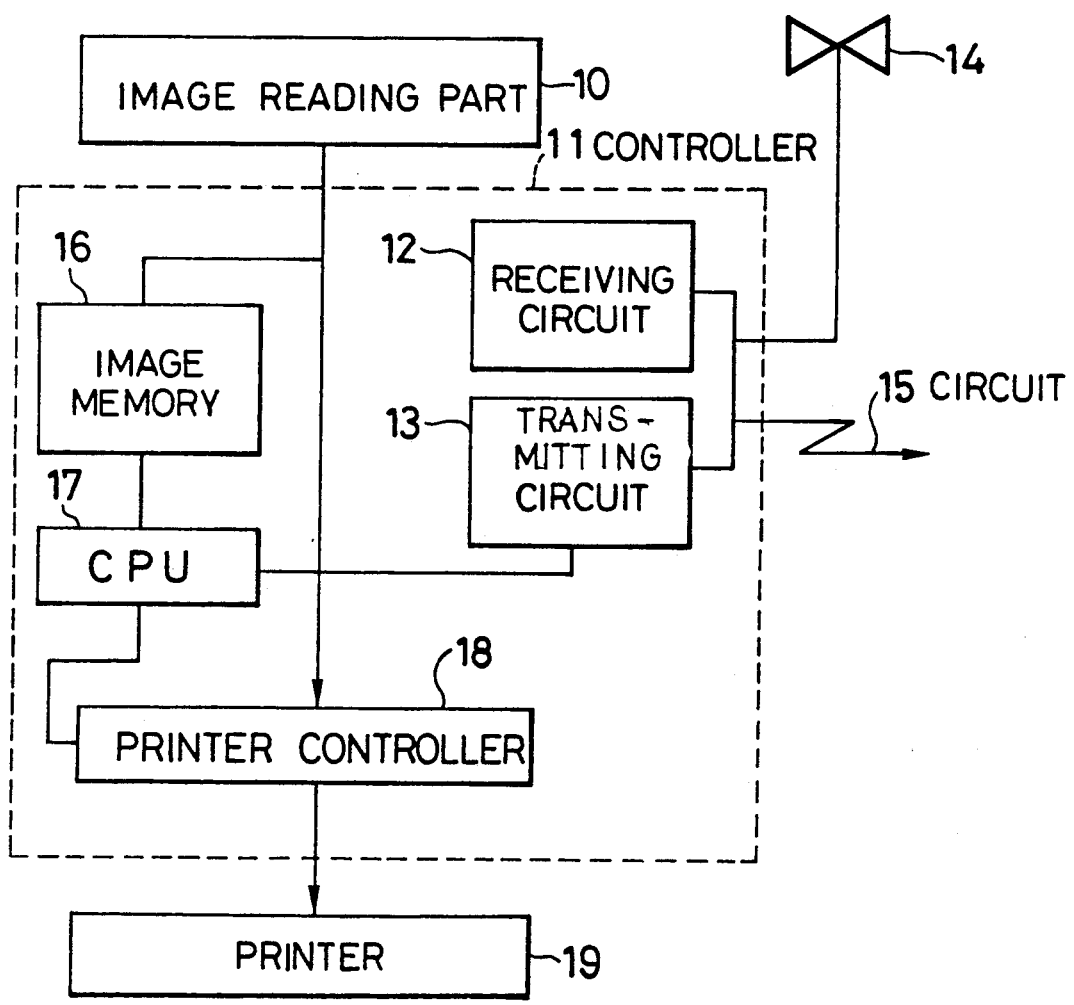
FIG. 2 is a block diagram of a facsimile system in which an electrophotographic apparatus comprised of an electrophotographic photosensitive member of the present invention is used as a printer.

When used as a printer of a facsimile system, the optical image exposing light L serves as exposing light used for the printing of received data. FIG. 2 illustrates an example thereof in the form of a block diagram.

In FIG. 2, a controller 11 controls an image reading part 10 and a printer 19. The whole of the controller 11 is controlled by CPU 17. Image data outputted from the image reading part is sent to the other facsimile station through a transmitting circuit. Data received from the other station is sent to a printer 19 through a receiving circuit 12. Given image data are stored in an image memory 16. A printer controller 18 controls the printer 19. The numeral 14 denotes a telephone.

An image received from a circuit 15 (image information from a remote terminal connected through the circuit) is demodulated in the receiving circuit 12, and then successively stored in an image memory 16 after the image information is decoded by the CPU 17. Then, when images for at least one page have been stored in the memory 16, the image recording for that page is carried out. The CPU 17 reads out the image information for one page from the memory 16 and sends the coded image information for one page to the printer controller 18. The printer controller 18, having received the image information for one page from the CPU 17, controls the printer 19 so that the image information for one page is recorded.

The CPU 17 receives image information for next page in the course of the recording by the printer 19.

Images are received and recorded in the above way.

EXAMPLES

The present invention will be described below in greater detail by giving Examples and Comparative Examples.

EXAMPLES I-1 to I-15

On an aluminum support, a solution obtained by dissolving 5 g of methoxymethylated nylon (number average molecular weight: 32,000) and 10 g of alcohol-soluble copolymer nylon (number average molecular weight: 29,000) in 95 g of methanol was coated by Mayer bar coating. A subbing layer was thus provided to have a dry coating thickness of 1.0 $\mu$m.

Next, 5 g of the compound of Compound I-(1) previously described was added in a solution obtained by dissolving 2 g of butyral resin (degree of butyralation: 63 mol %) in 95 g of cyclohexanone, and then dispersed for 2 hours using a sand mill. The resulting dispersion was coated by Mayer bar coating on the subbing layer previously formed, to have a dry coating thickness of 0.2 μm, followed by drying. A charge generation layer was thus formed.

Subsequently, 5 g of a hydrazone compound with the following structure:

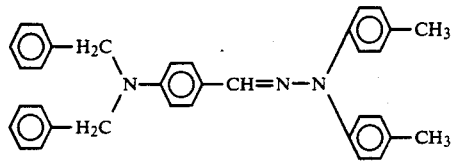

and 5 g of polymethyl methacrylate (number average molecular weight: 100,000) were dissolved in 40 g of chlorobenzene, and the resulting solution was coated by Mayer bar coating on the charge generation layer, followed by drying to form a charge transport layer with a thickness of 20 μm. An electrophotographic photosensitive member of Examle I-1 was thus prepared.

Electrophotographic photosensitive members corresponding to Examples I-2 to I-15 were prepared in the same manner as in the above, except for using other exemplary compounds in place of the compound of Compound I-(1).

The electrophotographic photosensitive members thus prepared were each negatively charged by corona charging at $-5$ kV, using an electrostatic copy paper tester (Model SP-428, manufactured by Kawaguchi Denki K. K.), which was left to stand in the dark place for 1 second, and then exposed to light at an illuminance of 10 lux using a halogen lamp. Charge characteristics were evaluated.

Surface potential ($V_0$), and amount of exposure ($E_{\frac{1}{2}}$) necessary for decaying to $\frac{1}{2}$ the surface potential after the photosensitive member was left to stand in the dark were measured as the charge characteristics. Results obtained are shown below.

| Example | Compound | $V_0$ (−V) | $E_{\frac{1}{2}}$ (lux · sec) |
|---|---|---|---|
| I-1 | I-(1) | 720 | 1.21 |
| I-2 | I-(2) | 710 | 1.57 |
| I-3 | I-(3) | 650 | 3.60 |
| I-4 | I-(4) | 680 | 2.20 |
| I-5 | I-(5) | 660 | 4.14 |
| I-6 | I-(6) | 750 | 1.85 |
| I-7 | I-(7) | 730 | 1.21 |
| I-8 | I-(8) | 700 | 3.02 |
| I-9 | I-(9) | 700 | 1.56 |
| I-10 | I-(10) | 690 | 1.90 |
| I-11 | I-(11) | 780 | 3.97 |
| I-12 | I-(12) | 760 | 4.09 |
| I-13 | I-(13) | 720 | 1.39 |
| I-14 | I-(14) | 650 | 1.69 |
| I-15 | I-(15) | 650 | 2.02 |

COMPARATIVE EXAMPLE I-1

An electrophotographic photosensitive member was prepared in entirely the same manner as in Example I-1, except that the compound of Compound I-(1) used therein was replaced with the compound of the following structure. Charge characteristics were similarly evaluated.

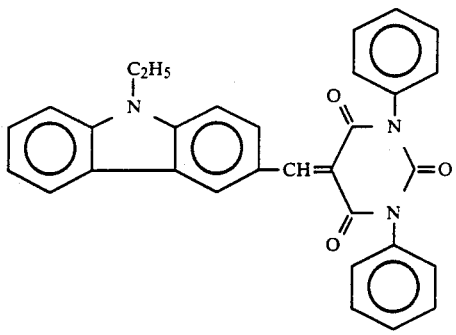

$V_0$: −850 V
$E_{\frac{1}{2}}$: 19.8 lux.sec

It is seen from Examples and Comparative Examples that the electrophotographic photosensitive members of the present invention all have sufficient chargeability and superior sensitivity.

EXAMPLES I-16 to I-20

Using the electrophotographic photosensitive member prepared in Example I-1, variations of light portion potential and dark portion potential in repeated use were measured.

As a method thereof, the above electrophotographic photosensitive member was stuck on a cylinder of an electrophotographic copying machine equipped with a corona charger of −6.5 kV, and exposure optical system, a developing unit, a transfer charger, a charge removing exposure optical system and a cleaner.

Initial dark portion potential ($V_D$) and light portion potential ($V_L$) were set around −700 V and −200 V, respectively, and the amount of variations of dark portion potential ($\Delta V_D$) and amount of variations of light portion potential ($\Delta V_L$) during the repeated use for 5,000 times were measured. Results are shown in the following table.

Similar evaluation was also made on the photosensitive members prepared in Examples I-6, I-7, I-9 and I-11.

Instances corresponding to the photosensitive members of Examples I-1, I-6, I-7, I-9 and I-11 are designated as Examples I-16, I-17, I-18, I-19 and I-20, respectively.

A negative symbol in the amount of variations of the potential represents a decrease in the absolute value of potential. A positive symbol represents an increase in the absolute value of the potential.

| Example | Photosensitive member (Example) | $\Delta V_D$ (V) | $\Delta V_L$ (V) |
|---|---|---|---|
| I-16 | I-1 | −15 | +20 |
| I-17 | I-6 | +5 | +5 |
| I-18 | I-7 | −20 | +10 |
| I-19 | I-9 | 0 | +5 |
| I-20 | I-11 | −20 | +5 |

COMPARATIVE EXAMPLE I-2

On the electrophotographic photosensitive member used in Comparative Example I-1, potential variations in repeated use were measured in the same manner as in Example I-16. Results are shown below.

$\Delta V_D$: −215 V
$\Delta V_L$: +105 V

It is seen from the above results that the electrophotographic photosensitive members of the present invention undergo less potential variations in repeated use.

EXAMPLE I-21

On the aluminum surface of an aluminum-deposited polyethylene terephthalate film, a subbing layer comprised of polyvinyl alcohol was formed with a coating thickness of 0.5 μm.

On the resulting subbing layer, a dispersion comprised of the compound of Compound I-(2) used in Example I-2 was coated by Mayer bar coating to give a dry coating thickness of 0.2 μm, followed by drying. A charge generation layer was thus formed.

Next, a solution obtained by dissolving 5 g of a styryl compound represented by the following structural formula:

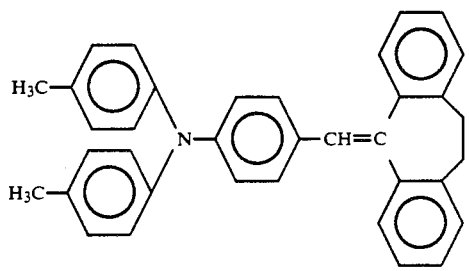

and 5 g of polycarbonate (weight average molecular weight: 55,000) in 40 g of tetrahydrofuran was coated on the charge generation layer to give a dry coating thickness of 20 μm, followed by drying. A charge transport layer was thus formed.

Charge characteristics and durability characteristics of the electrophotographic photosensitive member thus prepared were measured in the same manner as in Examples I-1 and I-13. Results obtained are shown below.

$V_0$: 720 V
$E_{\frac{1}{2}}$: 1.09 lux.sec
$\Delta V_D$: −15 V
$\Delta V_L$: +10 V

EXAMPLE I-22

An electrophotographic photosensitive member was prepared in which the charge generation layer and the charge transport layer of the photosensitive member of Example I-21 were coated and laminated in a reverse order. Charge characteristics thereof was evaluated in the same manner as in Example I-1, provided that the photosensitive member was positively charged.

Results obtained are shown below.
$V_0$: −700 V
$E_{\frac{1}{2}}$: 3.26 lux.sec
$E_{\frac{1}{4}}$: 3.9 lux.sec

EXAMPLES II-1 to II-12

On an aluminum support, a solution obtained by dissolving 5 g of methoxymethylated nylon (number average molecular weight: 32,000) and 10 g of alcohol-soluble copolymer nylon (number average molecular weight: 29,000) in 95 g of methanol was coated by Mayer bar coating. A subbing layer was thus provided to have a dry coating thickness of 1.0 μm.

Next, 5 g of the compound of Compound II-(1) previously described was added in a solution obtained by dissolving 2 g of butyral resin (degree of butyralation: 63 mol %) in 95 g of cyclohexanone, and then dispersed for 2 hours using a sand mill. The resulting dispersion was coated by Mayer bar coating on the subbing layer previously formed, to have a dry coating thickness of 0.2 μm, followed by drying. A charge generation layer was thus formed.

Subsequently, 5 g of a hydrazone compound with the following structure:

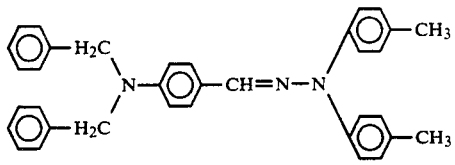

and 5 g of polymethyl methacrylate (number average molecular weight: 100,000) were dissolved in 40 g of chlorobenzene, and the resulting solution was coated by Mayer bar coating on the charge generation layer, followed by drying to form a charge transport layer with a thickness of 20 μm. An electrophotographic photosensitive member of Example II-1 was thus prepared.

Electrophotographic photosensitive members corresponding to Examples II-2 to II-12 were prepared in the same manner as in the above, except for using other exemplary compounds in place of the compound of Compound II-(1).

The electrophotographic photosensitive members thus prepared were each negatively charged by corona charging at −5 kV, using an electrostatic copy paper tester (Model SP-428, manufactured by Kawaguchi Denki K. K.), which was left to stand in the dark for 1 second, and then exposed to light at an illuminance of 10 lux using a halogen lamp. Charge characteristics were evaluated.

Surface potential ($V_0$), and amount of exposure ($E_{\frac{1}{2}}$) necessary for decaying to ½ the surface potential after the photosensitive member was left to stand in the dark were measured as the charge characteristics. Results obtained are shown below.

| Example | Compound | $V_0$ (−V) | $E_{\frac{1}{2}}$ (lux · sec) |
|---|---|---|---|
| II-1 | II-(1) | 650 | 2.65 |
| II-2 | II-(2) | 720 | 2.32 |
| II-3 | II-(3) | 750 | 4.91 |
| II-4 | II-(4) | 700 | 2.01 |
| II-5 | II-(5) | 710 | 3.10 |
| II-6 | II-(6) | 680 | 3.09 |
| II-7 | II-(7) | 640 | 4.21 |
| II-8 | II-(8) | 660 | 4.87 |
| II-9 | II-(9) | 680 | 3.63 |
| II-10 | II-(10) | 720 | 3.21 |
| II-11 | II-(11) | 730 | 3.52 |
| II-12 | II-(12) | 690 | 3.52 |

COMPARATIVE EXAMPLE II—1

An electrophotographic photosensitive member was prepared in entirely the same manner as in Example II-1, except that the compound of Compound II-(1) used therein was replaced with the compound of the following structure. Charge characteristics were similarly evaluated.

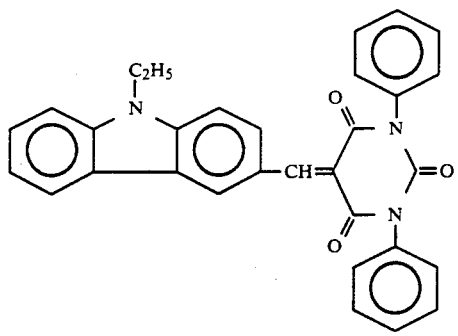

$V_0$: −850 V
$E_{\frac{1}{2}}$: 19.8 lux.sec

It is seen from Examples and Comparative Examples that the electrophotographic photosensitive members of the present invention all have sufficient chargeability and superior sensitivity.

EXAMPLES II-13 to II-17

Using the electrophotographic photosensitive member prepared in Example II-1, variations of light portion potential and dark portion potential during repeated use were measured.

As a method therefor, the above electrophotographic photosensitive member was stuck on a cylinder of an electrophotographic copying machine equipped with a corona charger of −6.8 kV, an exposure optical system, a developing unit, transfer charger, a charge removing exposure optical system and a cleaner.

Initial dark portion potential ($V_D$) and light portion potential ($V_L$) were set around −700 V and −200 V, respectively, and the amount of variations of dark portion potential ($\Delta V_D$) and amount of variations of light portion potential ($\Delta V_L$) during the repeated use for 5,000 times were measured. Results are shown in the following table.

Similar evaluation was also made on the photosensitive members prepared in Examples II-3, II-4, II-9 and II-11.

Instances corresponding to the photosensitive members of Examples II-1, II-3, II-4, II-9 and II-11 are designated as Examples II-13, II-14, II-15, II-16 and II-17, respectively.

A negative symbol in the amount of variations of the potential represents a decrease in the absolute value of potential. A positive symbol represents an increase in the absolute value of the potential.

| Example | Photosensitive member (Example) | $\Delta V_D$ (V) | $\Delta V_L$ (V) |
|---------|---------------------------------|------------------|------------------|
| II-13   | II-1                            | −10              | +20              |
| II-14   | II-3                            | 0                | +5               |
| II-15   | II-4                            | −20              | +15              |
| II-16   | II-9                            | −20              | +10              |
| II-17   | II-11                           | +5               | +10              |

COMPARATIVE EXAMPLE II-2

On the electrophotographic photosensitive member used in Comparative Example II-1, potential variations in repeated use were measured in the same manner as in Example II-13. Results are shown below.

$\Delta V_D$: −215 V
$\Delta V_L$: +105 V

It is seen from the above results that the electrophotographic photosensitive members of the present invention undergo less potential variations in repeated use.

EXAMPLE II-18

On the aluminum surface of an aluminum-deposited polyethylene terephthalate film, a subbing layer comprised of polyvinyl alcohol was formed with a coating thickness of 0.5 μm.

On the resulting subbing layer, a dispersion comprised of the compound of Compound II-(2) used in Example II-2 was coated by Mayer bar coating to give a dry coating thickness of 0.2 μm, followed by drying. A charge generation layer was thus formed.

Next, a solution obtained by dissolving 5 g of 38 styryl compound represented by the following structural formula:

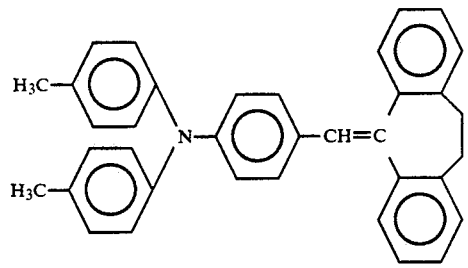

and 5 g of polycarbonate (weight average molecular weight: 55,000) in 40 g of tetrahydrofuran was coated on the charge generation layer to give a dry coating thickness of 20 μm, followed by drying. A charge transport layer was thus formed.

Charge characteristics and durability characteristics of the electrophotographic photosensitive member thus prepared were measured in the same manner as in Examples II-1 and II-13. Results obtained are shown below.

$V_0$: −720 V
$E_{\frac{1}{2}}$: 2.40 lux.sec
$\Delta V_D$: −10 V
$\Delta V_L$: +20 V

EXAMPLE II-19

An electrophotographic photosensitive member was prepared in which the charge generation layer and the charge transport layer of the photosensitive member prepared in Example II-18 were coated and laminated in a reverse order. Charge characteristics thereof was evaluated in the same manner as in Example II-1, provided that the photosensitive member was positively charged.

Results obtained are shown below.

$V_0$: +750 V
$E_{\frac{1}{2}}$: 3.61 lux.sec
$E_{\frac{1}{2}}$: 3.9 lux.sec

What is claimed is:

1. An electrophotographic photosensitive member comprising a conductive support and a photosensitive layer provided thereon, wherein said photosensitive layer contains at least one of the compounds of the following Formulas (I) and (II).

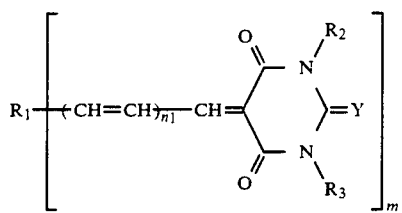

(I)

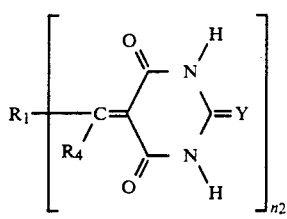

(II)

where Y represents an oxygen atom or a sulfur atom; $R_1$ represents a substituted or unsubstituted aromatic hydrocarbon group or aromatic heterocyclic group which may be bonded through a bonding group; $R_2$ and $R_3$ each represent a hydrogen atom, a substituted or unsubstituted alkyl group or aryl group; m is an integer of 1, 2 or 3; $n_1$ is an integer of 1, 2 or 3; $R_4$ represents a hydrogen atom, an alkyl group or a substituted or unsubstituted phenyl group; and $n_2$ is an integer of 1, 2 or 3.

2. An electrophotographic photosensitive member according to claim 1, wherein said compound represented by Formula (I) is selected from the group consisting of;

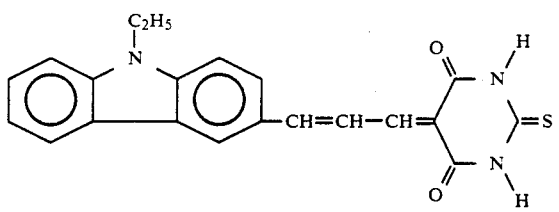

Compound I-(1)

Compound I-(2)

Compound I-(3)

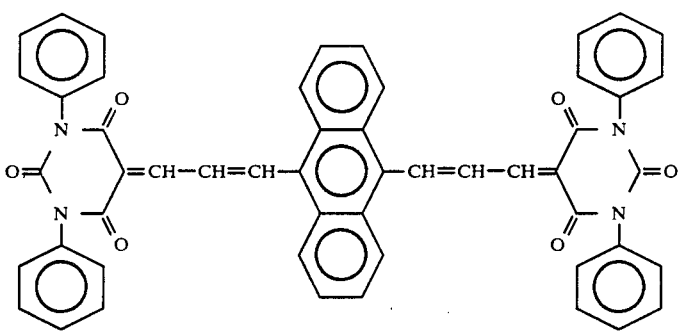

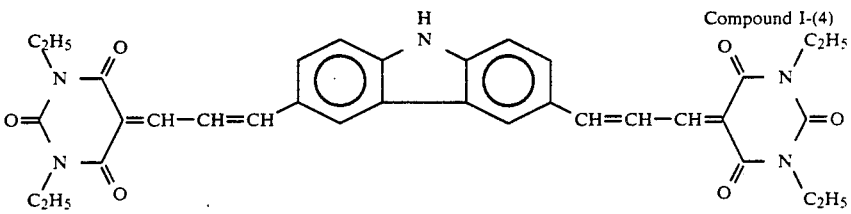

Compound I-(4)

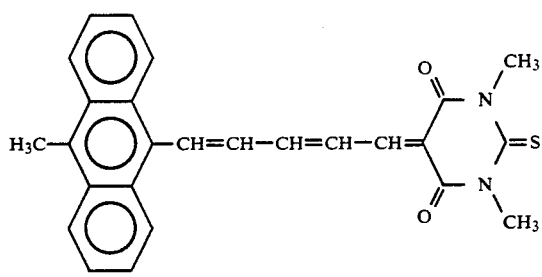
Compound I-(5)
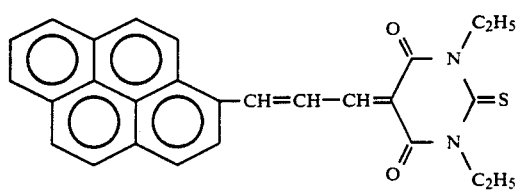
Compound I-(6)
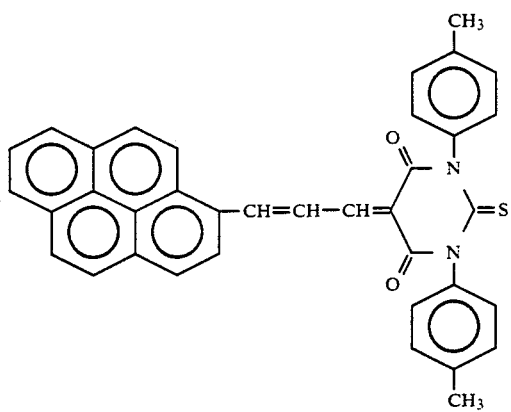
Compound I-(7)
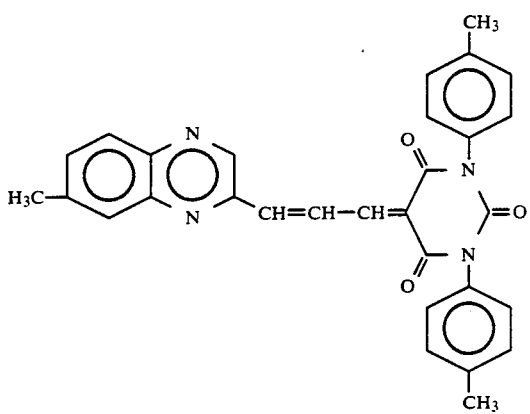
Compound I-(8)

Compound I-(9)
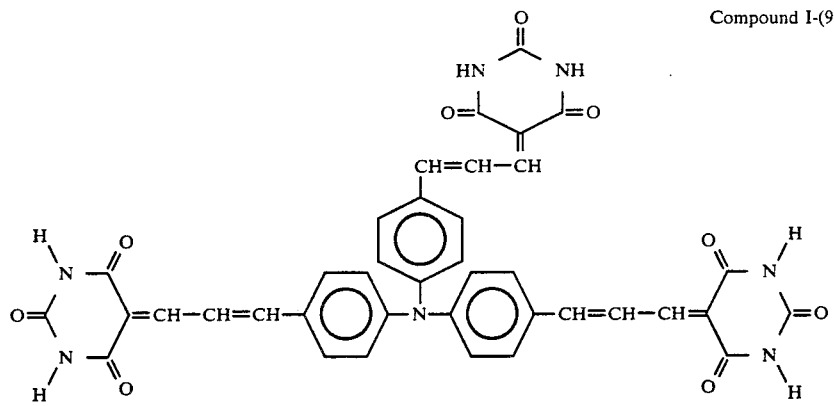
Compound I-(10)
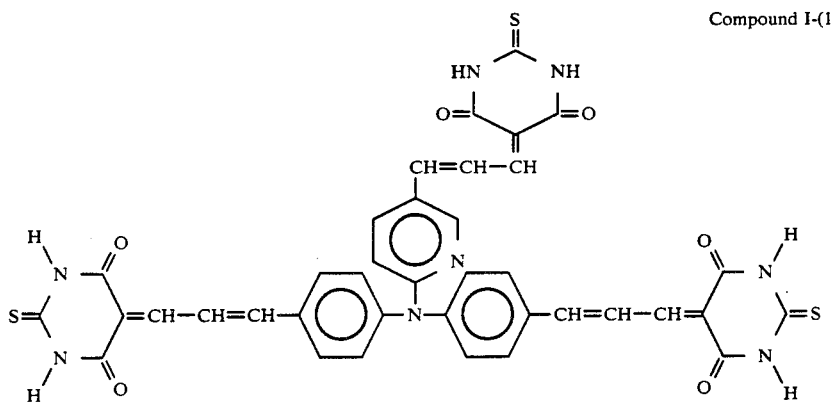
Compound I-(11)
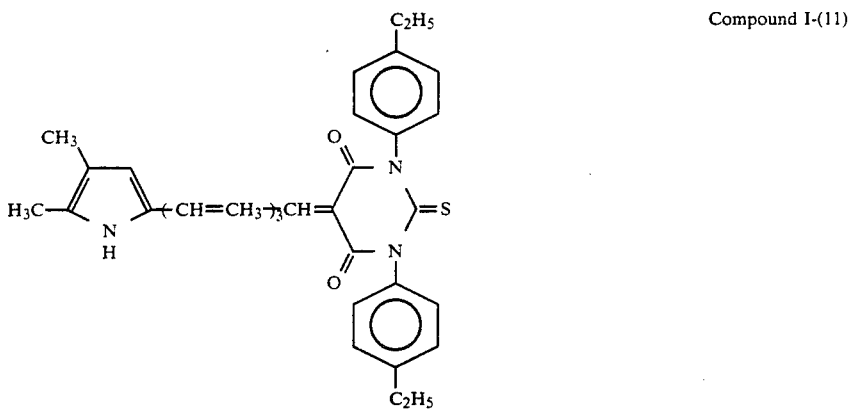
Compound I-(12)
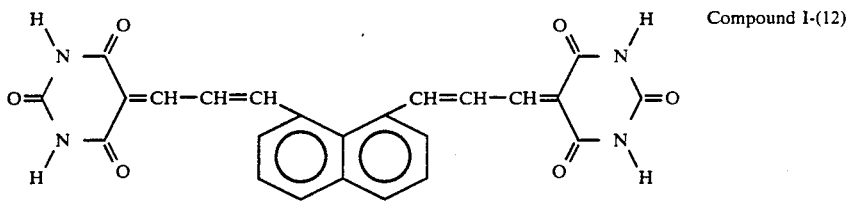
Compound I-(13)
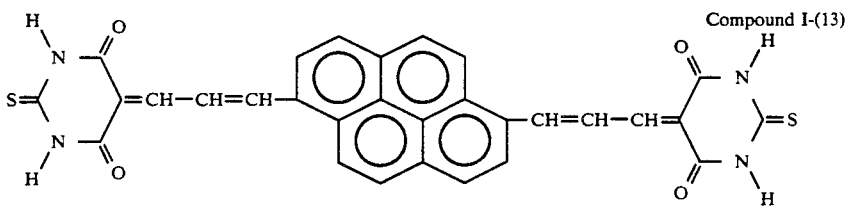

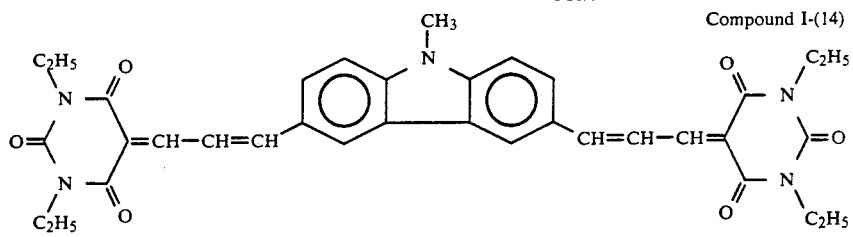
Compound I-(14)
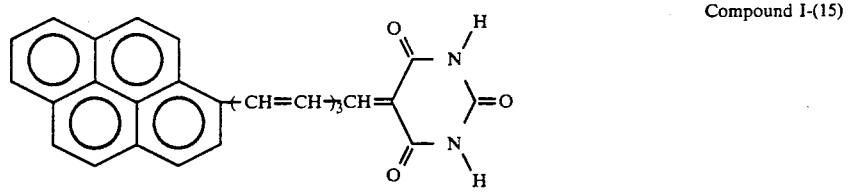
Compound I-(15)
3. An electrophotographic photosensitive member according to claim 1, wherein said compound represented by Formula (II) is selected from the group consisting of;
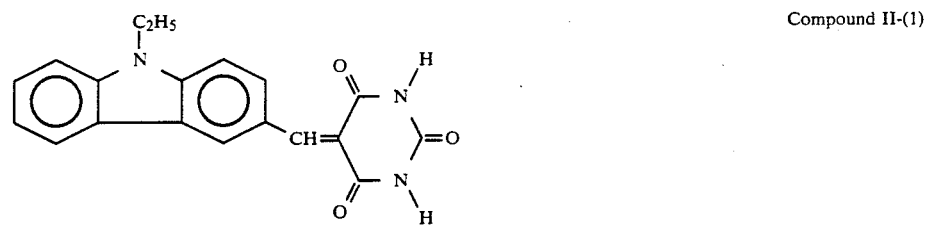
Compound II-(1)
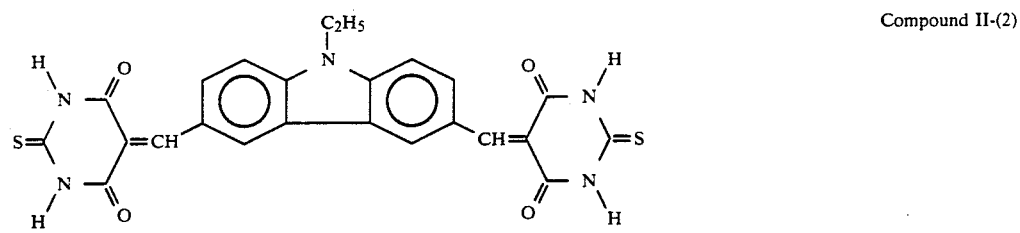
Compound II-(2)
Compound II-(3)
Compound II-(4)
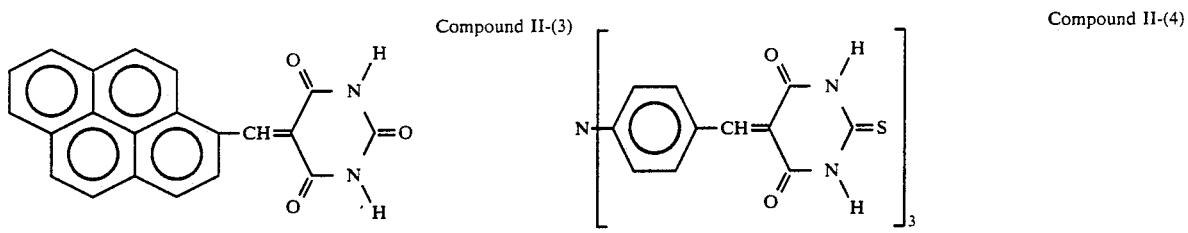
Compound II-(5)
Compound II-(6)
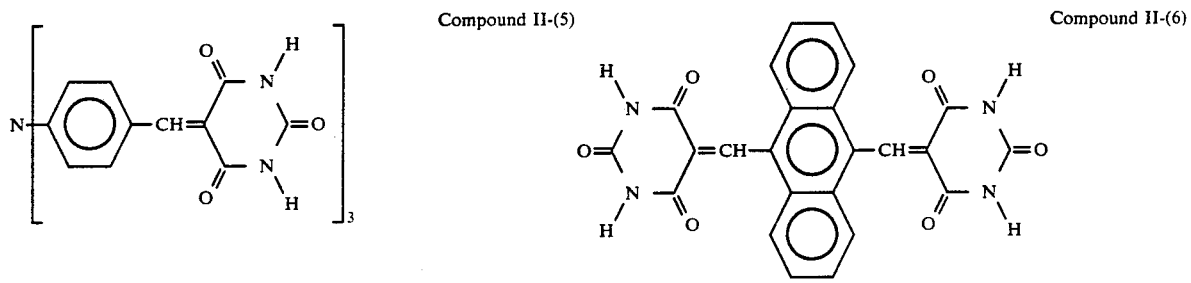

-continued

Compound II-(7) 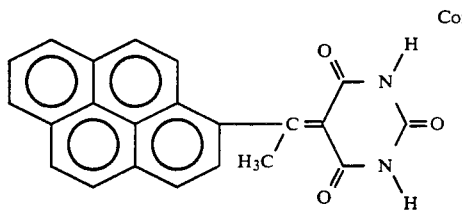

Compound II-(8) 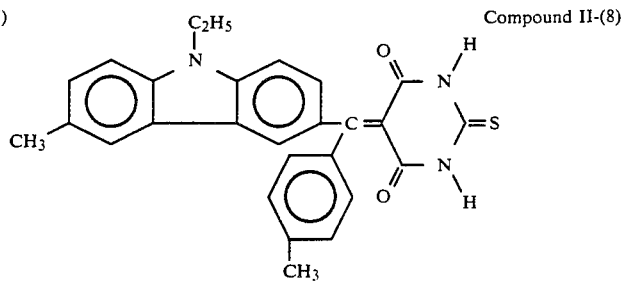

Compound II-(9) 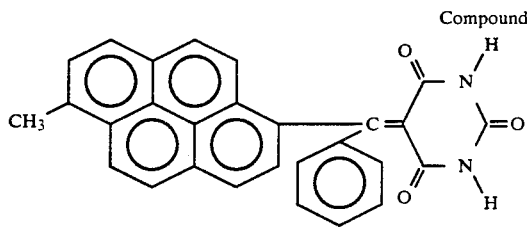

Compound II-(10) 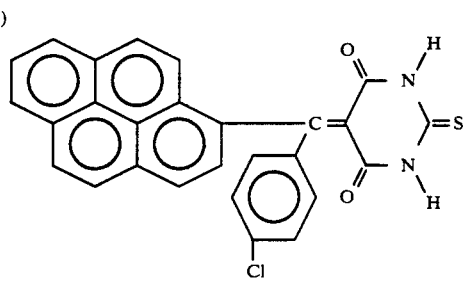

Compound II-(11) 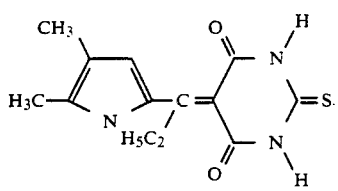

Compound II-(12) 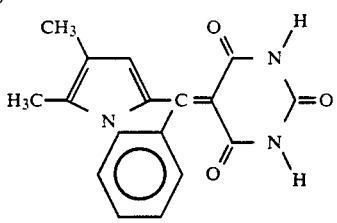

4. An electrophotographic photosensitive member according to claim 1, in which said photosensitivie layer comprises at least two layers of a charge generation layer containing at least one of the compounds of Formulas (I) and (II), and a charge transport layer.

5. An electrophotographic photosensitive member according to claim 2, in which said photosensitive layer comprises at least two layers of a charge generation layer containing at least one compound selected from the group consisting of Compounds I-(1) to I-(15), and a charge transport layer.

6. An electrophotographic photosensitive member according to claim 3, in which said photosensitive layer comprises at least two layers of a charge generation layer containing at least one compound selected from the group consisting of Compounds II-(1) to II-(12), and a charge transport layer.

7. An electrophotographic apparatus comprising:
an electrophotographic photosensitive member having a photosensitive layer containing at least one of the compounds of Formulas (I) and (II)

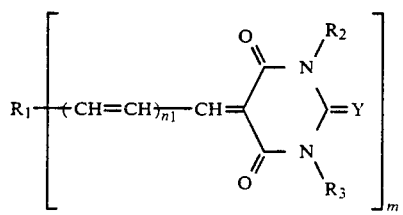 (I)

-continued

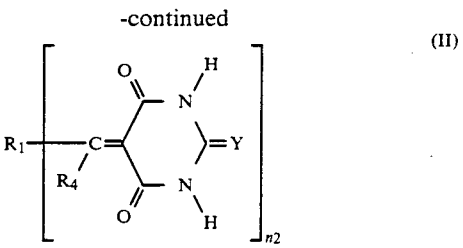 (II)

wherein Y represents an oxygen atom or a sulfur atom; $R_1$ represents a substituted or unsubstituted aromatic hydrocarbon group or aromatic heterocyclic group which may be bonded through a bonding group; $R_2$ and $R_3$ each represent a hydrogen atom, a substituted or unsubstituted alkyl group or aryl group; m is an integer of 1, 2 or 3; $n_1$ is an integer of 1, 2 or 3; $R_4$ represents a hydrogen atom, an alkyl group or a substituted or unsubstituted phenyl group; and $n_2$ is an integer of 1, 2 or 3; and
at least a charging means, a developing means and a cleaning means, provided around the electrophotographic photosensitive member.

8. A facsimile system comprising;
i) an electrophotographic apparatus comprising:
an electrophotographic photosensitive member having on a conductive support a photosensitive layer containing at least one of the compounds of Formulas (I) and (II)

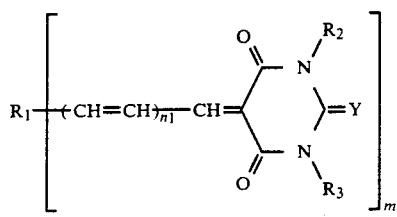

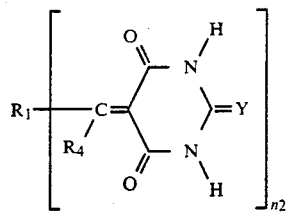

wherein Y represents an oxygen atom or a sulfur atom; $R_1$ respresents a substituted or unsubstituted aromatic hydrocarbon group or aromatic heterocyclic group which may be bonded through a bonding group; $R_2$ and $R_3$ each represent a hydrogen atom, a substituted or unsubstituted alkyl group or aryl group; m is an integer of 1, 2 or 3; $n_1$ is an integer of 1, 2 or 3; $R_4$ represents a hydrogen atom, an alkyl group or a substituted or unsubstituted phenyl group; and $n_2$ is an integer of 1, 2 or 3; and at least a charging means, a developing means and a cleaning means, provided around the electrophotographic photosensitive member; and ii) a means for receiving image information from a remote terminal.

* * * * *

UNITED STATES PATENT AND TRADEMARK OFFICE
CERTIFICATE OF CORRECTION

PATENT NO. : 5,126,222

DATED : June 30, 1992

INVENTOR(S) : KAZUSHI IUCHI, ET AL.

It is certified that error appears in the above-identified patent and that said Letters Patent is hereby corrected as shown below:

Title page,
item [30] FOREIGN APPLICATION PRIORITY DATA

"Jun. 12, 1989 [JP] Japan ........ 1-46864" should read
--Jun. 12, 1989 [JP] Japan ....... 1-146864--.

Title page,
item [57] ABSTRACT

Line 5, "Formula" should read --Formulas--.
Line 12, "$n_2$" should read --$n_1$--.

COLUMN 2

Line 44, "Formula" should read --Formulas--.

COLUMN 13

Line 21, "Formula" should read --Formulas--.

COLUMN 27

In Compound I-(11), "$CH=CH_3$" should read --$CH=CH$--.

UNITED STATES PATENT AND TRADEMARK OFFICE
CERTIFICATE OF CORRECTION

PATENT NO. : 5,126,222
DATED : June 30, 1992
INVENTOR(S) : KAZUSHI IUCHI, ET AL.

It is certified that error appears in the above-identified patent and that said Letters Patent is hereby corrected as shown below:

COLUMN 32

Line 63, "comprising;" should read --comprising:--.
Line 64, "comprising;" should read --comprising:--.
Line 68, "(II)" should read --(II),--.

Signed and Sealed this

Ninth Day of November, 1993

Attest:

BRUCE LEHMAN

*Attesting Officer*        *Commissioner of Patents and Trademarks*